(12) United States Patent
Jayaraman

(10) Patent No.: US 7,468,997 B2
(45) Date of Patent: Dec. 23, 2008

(54) SYSTEM FOR SWEPT SOURCE OPTICAL COHERENCE TOMOGRAPHY

(75) Inventor: Vijaysekhar Jayaraman, Goleta, CA (US)

(73) Assignee: Praevium Research, Inc., Santa Barbara, CA (US)

( * ) Notice: Subject to any disclaimer, the term of this patent is extended or adjusted under 35 U.S.C. 154(b) by 0 days.

(21) Appl. No.: 11/655,559

(22) Filed: Jan. 19, 2007

(65) Prior Publication Data

US 2007/0183643 A1     Aug. 9, 2007

Related U.S. Application Data

(60) Provisional application No. 60/760,544, filed on Jan. 20, 2006.

(51) Int. Cl.
*H01S 3/10* (2006.01)
*H01S 5/00* (2006.01)

(52) U.S. Cl. .................... 372/20; 372/50.124

(58) Field of Classification Search ............ 372/50.124, 372/20, 24, 99
See application file for complete search history.

(56) References Cited

U.S. PATENT DOCUMENTS

| | | | | |
|---|---|---|---|---|
| 5,877,038 | A * | 3/1999 | Coldren et al. ........... | 438/39 |
| 6,804,270 | B1 * | 10/2004 | Vakhshoori et al. ....... | 372/20 |
| 2002/0031155 | A1 * | 3/2002 | Tayebati et al. .......... | 372/50 |
| 2003/0031221 | A1 * | 2/2003 | Wang et al. .............. | 372/45 |
| 2007/0002327 | A1 * | 1/2007 | Zhou et al. .............. | 356/456 |

OTHER PUBLICATIONS

M.A.Choma,M.V.Sarunic,C.Yang,J.A.Izatt,"Sensitivity Advantage of Swept Source and Fourier Domain Optical Coherence . . . ,"Optics Express,vol. 11,No. 18,Sep. 8, 2003,p. 2183-2189.
J.Zhang,J.S.Nelson,Z.Chen,"Removal of a mirror image and enhancement of the signal to noise ratio in Fourier Domain Optical Coherence . . . ",Optics Lettersvol. 30,No. 2,Jan. 15, 2005.
M.A. Choma, K. Hsu, J.A. Izatt, "Swept Source Optical Coherence Tomography using an all-fiber 1300nm ring laser source," Journal of Biomedical Optics 10(4) Jul./Aug. 2005.
B.Mason,S.Lee,M.E.Heimbuch,L.A.Coldren,"Directly Modulated Sample Grating DBR Lasers for Long-Haul WDM . . . ," IEEE Photonics Technology Letters, vol. 9,No. 3,Mar. 1997,pp. 377-379.
Y,Matsui,D.Vakhshoori, et al,"Complete polarization mode control of long-wavelength tunable vertical . . . ",IEEE Journal of Quantum Electronics,vol. 39,No. 9,pp. 1037-1048,Sep. 2003.

(Continued)

Primary Examiner—Armando Rodriguez

(57) ABSTRACT

A swept source Optical coherence tomography system (SSOCT) comprises a vertical cavity surface-emitting laser with an integrated MEMs tunable mirror movable by electrostatic deflection. The MEMs tunable VCSEL offers scan rates greater than 100 khz and tuning ranges approaching 200 nm around 1300 nm and 150 nm around 850 nm. In the preferred embodiment of this invention, a bottom mirror of the VCSEL is comprised of a Aluminum Gallium Arsenide/Aluminum Oxide DBR stack, and a movable top mirror is comprised of a TiO2/SiO2 DBR stack. A MEMs tunable VCSEL at 1300 nm is preferably pumped through the top mirror in a wavelength range between 1050 and 1120 nm, and a MEMs tunable VCSEL at 850 nm is preferably pumped through the top mirror in a wavelength range between 700 nm and 730 nm.

6 Claims, 2 Drawing Sheets

OTHER PUBLICATIONS

G.D.Cole,J.E.Bowers, et al,"Dynamic Characterization of MEMs-Tunable . . . ," IEEE/LEOS Int'l Conf. on Optical MEMS & their Applications(MOEMS 2005), Oulu,Finland, Aug. 1-4, 2005.

H.Tabuchi,H.Ishikawa,"External grating tunable MQW laser with wide tuning range of 240nm," Electronic Letters, vol. 26, No. 11, 742-743, May 1990.

* cited by examiner

SYSTEM FOR SWEPT SOURCE OPTICAL COHERENCE TOMOGRAPHY

CROSS-REFERENCES TO RELATED APPLICATIONS

This application is entitled to the benefit of Provisional Patent Application Ser. No. 60/760,544, filed 2006, Jan. 20.

STATEMENT REGARDING FEDERALLY SPONSORED RESEARCH OR DEVELOPMENT

This invention was made under a government grant. The U.S. government may have rights in this invention.

BACKGROUND

1. Field of the Invention

This invention relates generally to optical coherence tomography and tunable lasers.

2. Description of Prior Art

Optical coherence tomography (OCT) is a technique for high-resolution depth profiling of a sample below the sample surface. OCT systems include a broadband light source, means for directing radiation from that light source to a reference mirror and to a sample, and means for detecting interference of light reflected from the reference mirror with light reflected from the sample. In time-domain OCT (TDOCT), the broadband light source is typically a superluminescent diode, which simultaneously emits multiple wavelengths, and the position of the reference mirror is scanned to depth profile the tissue. In swept source OCT (SSOCT), a tunable laser is employed as the broadband source. Here only one wavelength is present at any one time, and sweeping of the laser wavelength replaces mechanical scanning of the reference mirror. In recent years, SSOCT has become more widely employed, because of its theoretically demonstrated signal to noise ratio advantage over TDOCT, as described in (M. A. Choma, M. V. Sarunic, C. Yang, and J. A. Izatt, "Sensitivity Advantage of Swept Source and Fourier Domain Optical Coherence Tomography," *Optics Express*, vol. 11, no. 18, Sep. 8, 2003, p. 2183-2189.).

FIG. 1 illustrates a prior art SSOCT system. FIG. 1 employs a tunable source 100, which comprises a gain/cavity region 110, a bottom distributed Bragg reflector (DBR) mirror 120 and a top Fiber Fabry-Perot (FFP) mirror 130. An optical pump 140 pumps the tunable source 100, either through the mirrors or from the side. A tunable output radiation 150 of the tunable source 100 is split to a reference mirror 160 and to a sample 170, using a fiber coupler 180. Interference between light reflected from the reference mirror 160 and the sample 170 is detected by an optical detector 190. The optical power detected by 190 as a function of the wavelength of the radiation 150 is related by a Fourier transform to the depth profile of the sample reflectivity. The prior art configuration of FIG. 1 is described in detail in (J. Zhang, J. S. Nelson, and Z. Chen "Removal of a mirror image and enhancement of the signal to noise ratio in Fourier Domain Optical Coherence Tomography using an electro-optic phase modulator," *Optics Letters* vol. 30, no. 2, Jan. 15, 2005).

Other researchers have employed different means to achieve swept sources for SSOCT, including edge-emitting external cavity lasers, or a ring laser source tuned by a fiber Fabry-Perot filter, as in (Michael A. Choma, K. Hsu, and J. Izatt, "Swept Source Optical Coherence Tomography using an all-fiber 1300 nm ring laser source," *Journal of Biomedical Optics* 10(4) July/August 2005). All of the tunable lasers used in prior art SSOCT systems suffer from one or more of the following problems: slow wavelength scanning limited by mechanical constraints or long cavity lifetime, incomplete wavelength coverage, or limited tuning range. The scan rate for tuning schemes that employ FFP filters as one mirror of a cavity, for example, is limited to a few kilohertz (kHz). The limitation on scan rate ultimately leads to long image acquisition times, making the SS-OCT system less attractive for clinical use. Limited tuning range translates into limited spatial resolution, and incomplete wavelength coverage translates into more shallow depth information.

Aside from the tunable lasers described above, other candidate tunable lasers for SSOCT include widely tunable lasers designed for telecommunications. One example of such a laser is the sampled grating DBR (SGDBR) laser described in (B. Mason, S. Lee, M. E. Heimbuch, and L. A. Coldren, "Directly Modulated Sampled Grating DBR Lasers for Long-Haul WDM Communication Systems," *IEEE Photonics Technology Letters*, vol. 9, no. 3, March 1997, pp. 377-379). The SGDBR is a multi-section laser requiring control of 4 electrodes to set the wavelengths. The wavelength is a complex and non-monotonic function of these wavelengths, and this laser is not suitable for the kind of linear or sinusoidal wavelength sweeping required in SSOCT systems.

From the foregoing, it is clear that what is required is an SS-OCT system employing a tunable laser with wide tuning range, wavelength scan frequency greater than a few kHz, complete wavelength coverage over the tuning range, and wavelength tuning that is a simple monotonic function of a tuning control signal.

SUMMARY OF THE INVENTION

The present invention provides a swept source OCT system comprising a vertical cavity surface-emitting laser (VCSEL) with an integrated MEMs tunable mirror. The laser can have scan rates exceeding 100 kHz repetition frequency, and complete wavelength coverage over more than 100 nm. In the preferred embodiment of this system, the VCSEL has one mirror comprised of alternating layers of GaAs and Aluminum Oxide, and another mirror is comprised of an alternating dielectric stack of Titanium Dioxide (TiO2) and Silicon dioxide (SiO2) suspended on a deformable membrane. Additionally, the VCSEL is optically pumped by an edge-emitting laser, and comprises quantum wells of more than one composition or more than one quantum state to broaden the effective gain bandwidth of its active region.

One preferred embodiment of this invention employs a MEMs tunable VCSEL operating around 1300 nm, for subsurface imaging of human skin and other endoscopic applications, and another preferred embodiment of this invention employs a MEMs tunable VCSEL operating around 850 nm for in-vivo characterization of the human eye.

A further understanding of the nature and advantages of the present invention may be realized by reference to the remaining portions of the specifications and drawings.

REFERENCE NUMERALS IN DRAWINGS

Figure 1:
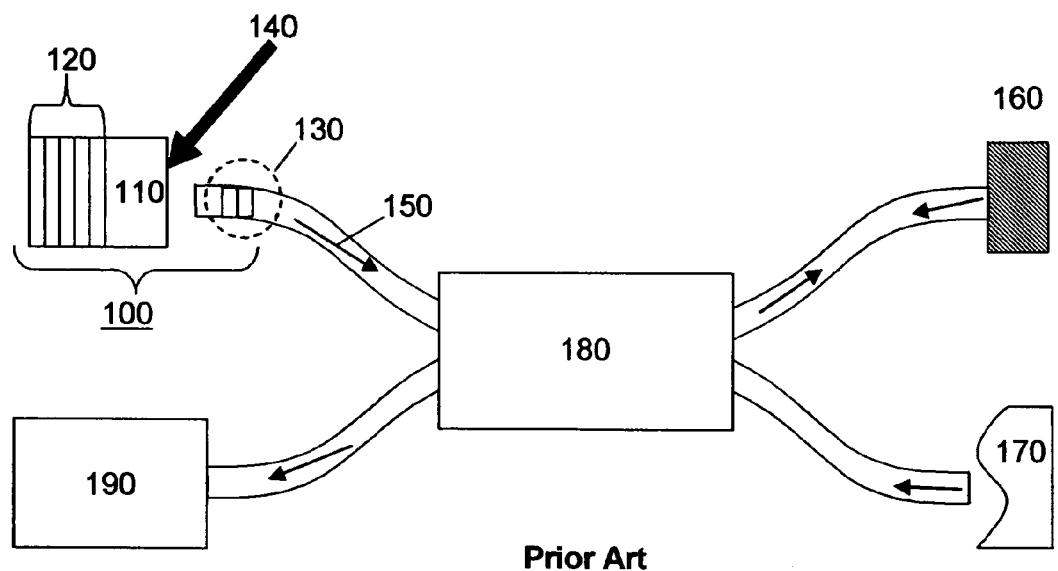
FIG. 1 is a schematic representation of a prior art SSOCT system employing a VCSEL with a fiber Fabry-Perot tunable filter.

100 Tunable VCSEL in prior art SSOCT system
110 VCSEL gain/cavity region in prior art SSOCT system
120 Bottom mirror in VCSEL in prior art SSOCT system
130 Top mirror in VCSEL of prior art SSOCT system
140 Optical pump beam in prior art SSOCT system
150 Tunable radiation in prior art SSOCT system
160 Reference mirror in prior art SSOCT system
170 Sample in prior art SSOCT system
200 MEMs tunable VCSEL in SSOCT system according to present invention
210 Gain/cavity region in SSOCT system according to present invention
220 Bottom VCSEL mirror in SSOCT system according to present invention
230 Top VCSEL mirror in SSOCT system according to present invention
235 VCSEL electrostatic actuator in SSOCT system according to present invention
240 Optical pump beam in SSOCT system according to present invention
245 WDM coupler in SSOCT system according to present invention
250 Tunable radiation in SSOCT system according to present invention
255 Input fiber in SSOCT system according to present invention
260 Reference mirror in SSOCT system according to present invention
270 Sample in SSOCT system according to present invention
280 Fiber coupler in SSOCT system according to present invention
290 Optical detector in SSOCT system according to present invention
295 Anti-reflection coating in MEMs tunable VCSEL in SSOCT system according to present invention
300 MEMs tunable VCSEL tuned to a first wavelength in SSOCT system according to present invention
310 MEMs tunable VCSEL tuned to a second wavelength in SSOCT system according to present invention
400 Airgap in MEMs tunable VCSEL tuned to first wavelength in SSOCT system according to present invention
410 Airgap in MEMs tunable VCSEL tuned to second wavelength in SSOCT system according to present invention

DETAILED DESCRIPTION OF PREFERRED AND ALTERNATE EMBODIMENTS

Figure 2:
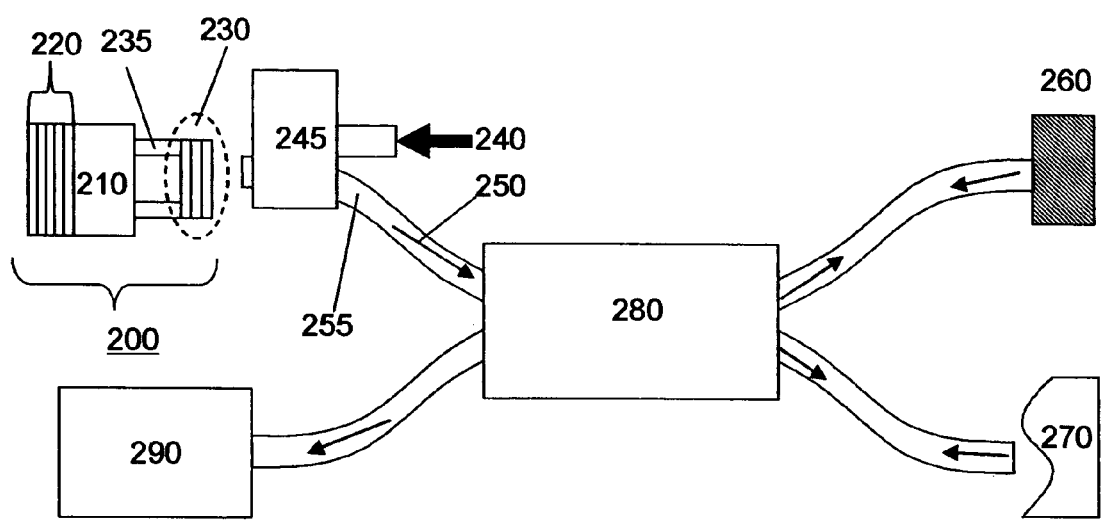
FIG. 2 is a schematic representation of the present invention employing a MEMs tunable VCSEL in an SSOCT system.

FIG. 2 shows a schematic of a preferred embodiment of the present invention. A tunable VCSEL 200 is comprised of a back mirror 220, a gain/cavity region 210, and a top mirror 230. The top mirror 230 sits on an electrostatic actuator 235, which enables electrostatic deflection of the top mirror 230. The combination of the mirror 230 and actuator 235 form an integrated tunable MEMs mirror for the VCSEL, which can be tuned by a voltage controlled deflection of the top mirror 230. A tunable emission 250 from the VCSEL 200 enters an input fiber 255, and is split to a reference mirror 260 and sample 270 by a fiber coupler 280. A pump beam 240 pumps the VCSEL 200 from the fiber 255 and through the top mirror 230. The pump 240 is coupled to the fiber 255 through a WDM coupler 245. Although having the pump enter through the top mirror 230 is preferable, alternate embodiments could employ pumping through the bottom mirror 220, or side pumping without passing through either mirror. Similarly, the VCSEL emission 250 could also be taken from the opposite side of the VCSEL cavity, through the mirror 220, instead of through the mirror 230.

Optically pumped MEMs tunable VCSELs have been described by other authors, such as in (Y. Matsui, D. Vakhshoori, P. D. Wang, P L Chen, C C Lu, M. Jiang, K. Knopp, S. Burroughs, and P. Tayebati, "Complete polarization mode control of long-wavelength tunable vertical cavity surface-emitting lasers over 65 nm tuning, up to 14-mW power," *IEEE Journal of Quantum Electronics*, vol. 39, no. 9, pp. 1037-1048, September 2003.) The combination of a MEMs tunable VCSEL and a swept source OCT system, however, has thus far not been proposed or described. This combination of technologies is critical to increasing the image acquisition rate of SSOCT systems, since current technologies are limited to a few Khz wavelength scan rate. Existing MEMs tunable VCSELs have also not been optimized, applied to, or designed for SSOCT systems, since the development of MEMs VCSELs has been fueled by telecommunications applications.

MEMs tunable VCSELs can be designed to have scan rates in excess of 100 khz, because of the short photon lifetime of a typical VCSEL cavity, and because of low mass of the mirror 230 relative to FFP mirrors or other types of mechanically tuned mirrors. Work described in (G. D. Cole, J. E. Bowers, K. L. Turner, and N. C. McDonald, "Dynamic Characterization of MEMs-Tunable Vertical-Cavity SOAs," IEEE/LEOS International Conference on Optical MEMS and Their Applications (MOEMS 2005), Oulu, Finland, 1-4 August 2005.) demonstrates MEMs resonance frequencies exceeding 160 kHz, with deflections of the sort needed for wide tuning range of VCSELs.

In a preferred embodiment of FIG. 2, the mirror 220 is an AluminumGallium Arsenide/Aluminum oxide (AlGaAs/AlxOy) mirror formed by lateral oxidation of an Aluminum Gallium Arsenide DBR mirror. At 1300 nm, the aluminum content of the non-oxidized mirror layers is zero, so after oxidation the mirror is a GaAs/AlxOy mirror. For 1300 nm operation, which is important in subsurface skin imaging, the gain/cavity region is preferably comprised of AlInGaAs/InP quantum wells, and is wafer-bonded to the DBR mirror 220. For 850 nm operation, which is important in in-vivo imaging of the human eye, the gain /cavity region 210 is preferably comprised of GaAs/AlGaAs and is epitaxially grown with the DBR mirror 220. The DBR mirror 220 is preferably comprised of $Al_{0.4}Ga_{0.6}As$/AlxOy after oxidation. The mirror 230, which is suspended on the actuator 235, is preferably a dielectric distributed Bragg reflector comprised of alternating layers of titanium dioxide and silicon dioxide. This mirror can be suspended on a thin layer of semiconductor, such as GaAs. Other dielectric mirror combinations are also possible. For 1300 nm operation, the optical pump 240 has a wavelength preferably in the range of 1050 nm to 1120 nm, and the pump beam enters through the suspended dielectric mirror 230. In this wavelength range, the titanium dioxide/silicon dioxide mirror has a number of low reflectivity nulls and the fully oxidized mirror 220 is still reflective, leading to a double-pass pumping situation. Similarly, the pump wavelength for 850 nm operation is preferably in the range of 650-780 nm, for the same reasons at the 1050-1120 nm range associated with pumping 1300 nm VCSELs.

Figure 3:
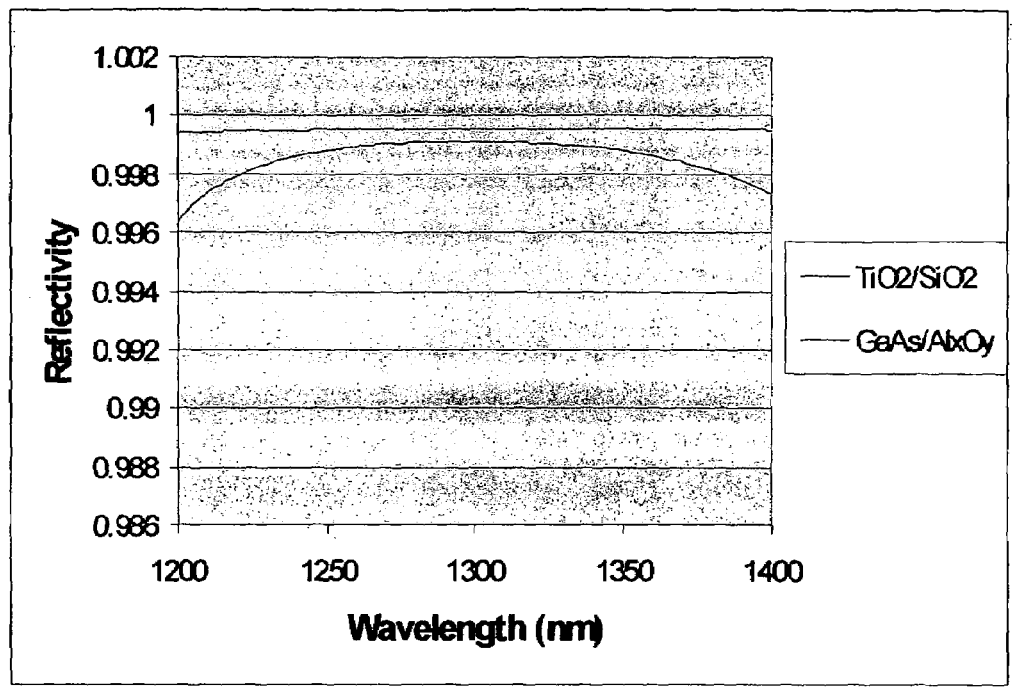
FIG. 3 is representation of mirror reflectivity of GaAs/AlxOy mirror and a SiO2/TiO2 mirror in a 200 nm range around 1300 nm.

The VCSEL 200 in the SSOCT system of FIG. 2 should ideally have a tuning range in excess of 100 nm in the vicinity of 1300 nm, since the imaging resolution of SSOCT systems varies inversely with the tuning range of the swept source. Prior art MEMs VCSELs have shown tuning ranges up to 64 nm around 1550 nm, as described in (Y. Matsui, D. Vakhshoori, P. D. Wang, P L Chen, C C Lu, M. Jiang, K. Knopp, S. Burroughs, and P. Tayebati, "Complete polarization mode control of long-wavelength tunable vertical cavity surface-emitting lasers over 65 nm tuning, up to 14-mW power," *IEEE Journal of Quantum Electronics*, vol. 39, no. 9, pp. 1037-1048, September 2003.). Obtaining tuning range of >100 nm requires broad bandwidth for the back mirror 220 and suspended mirror 230, and a broad spectrum of available gain for the active region. The choice of an Aluminum Gallium Arsenide/Aluminum oxide mirror for 220 and TiO2/SiO2 mirror for 230, already indicated as preferable in the paragraphs above, guarantees that there is sufficient mirror reflectivity over 200 nm tuning range around 1300 nm. This is illustrated in FIG. 3, which plots reflectivity of a 9 period TiO2/SiO2 mirror and a 6 period GaAs/AlxOy mirror over 200 nm near 1300 nm. As can be seen, the roundtrip loss through both mirrors is less than 0.004 for the entire 200 nm range. Well-known gain curves for 1300 nm gain regions indicate that with 3 or more quantum wells, it is possible to obtain roundtrip gains approaching 0.01, especially when well-known periodic gain techniques are use. Thus, the feasibility of lasing operation over 200 nm is not prevented by mirror reflectivity considerations, if the proper choice of mirrors is made. Additionally, prior researchers such as (H. Tabuchi and H. Ishikawa, "External grating tunable MQW laser with wide tuning range of 240 nm," Electronics Letters, vol. 26, no. 11, 742-743, May 1990.), have shown lasing gain over a 240 nm range at 1550 nm, using a quantum well active region with intentional introduction of a second quantum state. It is well-known that 1300 nm gain regions are similar to 1550 nm gain regions, so introduction of a second quantum state will enable 200 nm gain bandwidth in 1300 nm VCSELs. Gain bandwidth of the active region can also be further enhanced by introduction of varying width or varying composition quantum wells.

Figure 4:
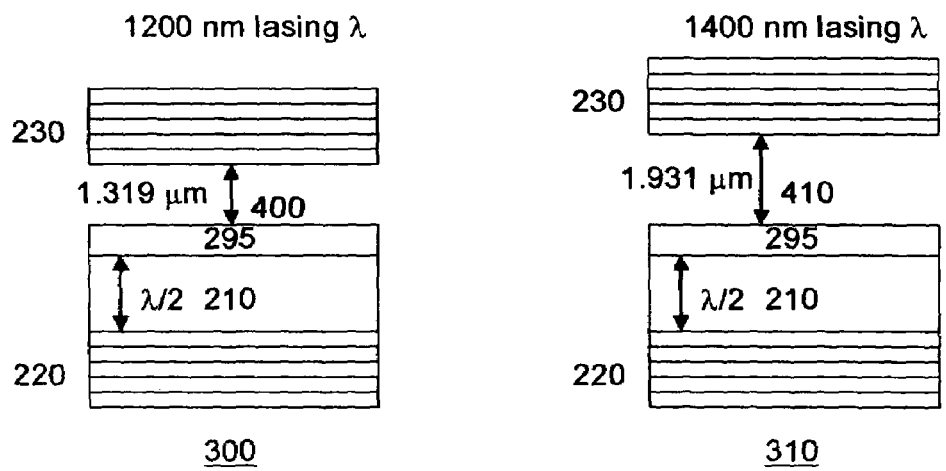
FIG. 4 is a schematic representation of the MEMs tunable VCSEL in FIG. 2 tuned to two different wavelengths.

Given that an optically pumped VCSEL cavity with the chosen mirrors and a properly designed active region can support lasing over >200 nm, it is instructive to calculate the amount of MEMs mirror deflection required to achieve this tuning. FIG. 4 illustrates a representative VCSEL design tuned to two extremes of the tuning range. This VCSEL consists of a GaAs/AlxOy bottom DBR 220, a TiO2/SiO2 top DBR 230, a gain/cavity region 210 which is ½ wavelength thick, and an anti-reflection coating 295. When the VCSEL is in a tuning state 300, an airgap 400 is 1.319 microns thick, leading to a calculated lasing wavelength of 1200 nm. When the VCSEL is in a tuning state 310, an airgap 410 is 1.931 microns thick, leading to a calculated lasing wavelength of 1400 nm. Thus, the example design of FIG. 4 requires 0.612 microns of mirror deflection to achieve 200 nm tuning range. This range of mirror deflections has been demonstrated in (G. D. Cole, J. E. Bowers, K. L. Turner, and N. C. McDonald, "Dynamic Characterization of MEMs-Tunable Vertical-Cavity SOAs," IEEE/LEOS International Conference on Optical MEMS and Their Applications (MOEMS 2005), Oulu, Finland, 1-4 August 2005.), at frequencies exceeding 150 khz, so the VCSEL design presented here can feasibly achieve 200 nm tuning at high scan rates.

Those skilled in the art of VCSELs can perform similar calculations at 850 nm, and conclude that with similar mirror technologies—TiO2/SiO2 and AlGaAs/AlxOy—it is possible to achieve 150 nm tuning ranges with smaller mirror deflections. Thus the invention presented here is applicable to a number of wavelength ranges, although the 850 nm range and the 1300 nm range are preferred because of the known applications at these wavelengths.

While this invention has been particularly shown and described with references to preferred and alternate embodiments thereof, it will be understood by those skilled in the art that various changes in form and details may be made therein without departing from the spirit and scope of the invention as defined by the appended claims.

What is claimed is:

1. A system for swept source optical coherence tomography, the system comprising A vertical cavity laser with an on-chip integrated MEMs tunable mirror, and operative to emit tunable radiation having an emission wavelength, Means for directing said tunable radiation to a reference mirror and to a sample, and An optical detector for detecting an interference between light reflected from said reference mirror and said sample, Wherein said vertical cavity laser has a wavelength scan repetition rate of greater than about 100 kHz.

2. The system of claim 1, wherein said vertical cavity laser is scanned at a frequency substantially equal to a mechanical resonance frequency of said MEMs tunable mirror.

3. The system of claim 1, wherein at least one mirror of said vertical cavity laser includes alternating layers of GaAs and Aluminum Oxide.

4. The system of claim 1, wherein at least one mirror of said vertical cavity laser includes alternating layers of TiO2 and SiO2.

5. The system of claim 1, wherein said emission wavelength is tuned within a range from about 1200 nm to about 1400 nm.

6. The system of claim 1, wherein said emission wavelength is tuned within a range from about 775 nm to about 925 nm.

* * * * *

UNITED STATES PATENT AND TRADEMARK OFFICE
CERTIFICATE OF CORRECTION

PATENT NO. : 7,468,997 B2  
APPLICATION NO. : 11/655559  
DATED : December 23, 2008  
INVENTOR(S) : Vijaysekhar Jayaraman Page 1 of 1

It is certified that error appears in the above-identified patent and that said Letters Patent is hereby corrected as shown below:

Page 1, lines 11-12 of specification change

"This invention was made under a government grant. The U.S. government may have rights in this invention."

To:

"This invention was made under U.S. government grant R44CA101067. The U.S. government has certain rights in this invention."

Signed and Sealed this

Twenty-fifth Day of May, 2010

David J. Kappos
*Director of the United States Patent and Trademark Office*